United States Patent
Weers

(10) Patent No.: US 10,633,601 B2
(45) Date of Patent: Apr. 28, 2020

(54) NITROGEN-FREE HYDROGEN SULFIDE SCAVENGERS

(71) Applicant: Baker Hughes, a GE company, LLC, Houston, TX (US)

(72) Inventor: Jerry J. Weers, Richmond, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 243 days.

(21) Appl. No.: 15/815,203

(22) Filed: Nov. 16, 2017

(65) Prior Publication Data

US 2019/0144761 A1 May 16, 2019

(51) Int. Cl.
*C10G 29/22* (2006.01)
*C10G 21/16* (2006.01)
*C07C 69/96* (2006.01)
*C07C 7/20* (2006.01)

(52) U.S. Cl.
CPC .............. *C10G 29/22* (2013.01); *C07C 7/20* (2013.01); *C07C 69/96* (2013.01); *C10G 21/16* (2013.01); *C10G 2300/1025* (2013.01); *C10G 2300/1037* (2013.01); *C10G 2300/207* (2013.01); *C10G 2300/44* (2013.01); *C10G 2300/802* (2013.01)

(58) Field of Classification Search
CPC .. C10G 29/22; C10G 21/16; C10G 2300/207; C10G 2300/44; C10G 2300/1037; C10G 2300/1025; C10G 2300/802; C07C 69/96; C07C 7/20
See application file for complete search history.

(56) References Cited

U.S. PATENT DOCUMENTS

| | | | |
|---|---|---|---|
| 3,928,211 A | 12/1975 | Browning et al. | |
| 4,410,432 A | 10/1983 | Domahidy | |
| 5,980,845 A | 11/1999 | Cherry | |
| 8,075,803 B2 | 12/2011 | Kalb et al. | |
| 8,366,914 B2 | 2/2013 | Yang et al. | |
| 8,523,994 B2 | 9/2013 | Draper et al. | |
| 8,596,364 B2 | 12/2013 | Horton et al. | |
| 2015/0093313 A1* | 4/2015 | Broderick | B01D 53/526 423/226 |

OTHER PUBLICATIONS

Amosa et al, Sulfide Scavengers in Oil and Gas Industry, (2010), NAFTA 61 (2), 85-92 (Year: 2010).*
Selva, Maurizio, et al., "Ionic liquids as transesterification catalysts: applications for the synthesis of linear and cyclic organic carbonates", Beilstein Journal of Organic Chemistry, 2016, 12, 1911-1924.
Taylor, G.N., et al., "Fresh Insight into the H2S Scavenging Mechanism of MEA-Triazine vs. MMA-Triazine", SPE184529-MS, Jan. 10, 2017.
Cella, James A., et al., "Preparation of Dialkyl Carbonates via the Phase-Transfer-Catalyzed Alkylation of Alkali Metal Carbonate and Bicarbonate Salts", J. Org. Chem, 49, 1984, 1122-1125.
Verdecchia, Mirella, et al., "A Safe and Mild Synthesis of Organic Carbonates from Alkyl Halides and Tetrabutylammonium Alkyl Carbonates", J. Org. Chem. 67, 2002, 8287-8289.
Huntsman Corporation Brochure, JEFFSOL Alkylene Carbonates, 2001, 36 pages.
Amosa, M.K., et al., "Sulphide Scavengers in Oil and Gas Industry—A Review", NAFTA, 61. 2010, 85-92.

* cited by examiner

*Primary Examiner* — Randy Boyer
*Assistant Examiner* — Juan C Valencia
(74) *Attorney, Agent, or Firm* — Mossman, Kumar & Tyler, P.C.

(57) ABSTRACT

Treatment of streams containing hydrogen and/or hydrocarbons, and in one non-limiting embodiment refinery distillates, with alkyl carbonates, such as dimethylcarbonate, alone or together with at least one solvent results in reduction or removal of hydrogen sulfide ($H_2S$) that is present to give easily removed alkyl sulfides and/or mercaptans. In one non-limiting embodiment, the treatment converts the original hydrogen sulfide into alkyl sulfides and/or mercaptans that can be extracted from the stream with caustic solutions, mercaptan scavengers, solid absorbents such as clay or activated carbon or liquid absorbents such as amine-aldehyde condensates and/or aqueous aldehydes.

19 Claims, No Drawings

NITROGEN-FREE HYDROGEN SULFIDE SCAVENGERS

TECHNICAL FIELD

The present invention relates to the removal of hydrogen sulfide ($H_2S$) from streams containing hydrogen and/or hydrocarbons, and more particularly relates, in one non-limiting embodiment, to methods for removing $H_2S$ from such streams using an alkyl carbonate.

TECHNICAL BACKGROUND

The removal of hydrogen sulfide and other sulfur species from hydrocarbon fluids and aqueous streams in oil and gas production and refining is important because of the many safety and environmental hazards posed by the presence of such species.

For example, during combustion, sulfur-rich hydrocarbon streams produce heavy environmental pollution. Further, when sulfur-rich streams contact metals, sulfur species lead to brittleness in carbon steels and to stress corrosion cracking in more highly alloyed metals used in oil and gas production and refining operations. Moreover, hydrogen sulfide in various hydrocarbon or aqueous streams poses an environmental hazard if the hydrogen sulfide in these streams is released into the air or water sources.

Triazine and glyoxal are two of the most widely used hydrogen sulfide scavengers. However, using these compounds often results in the formation of oligomeric and polymeric sulfur-containing structures that instigates deposit build-up in the system. Removal of these solids may be difficult and oftentimes results in lost operational time. For example, use of triazines can result in the formation of dithiazines, especially at colder conditions. Triazines react quickly in aqueous environments but disperse poorly in crude oil conditions, thus slowing down reaction kinetics. In crude oil conditions, triazine is spent at a very high level where amorphous dithiazine will most likely form. Thus, in many applications the use of nitrogen-containing additives such as triazines and other amines is undesirable.

Thus, generally sulfur, in the form of $H_2S$, is an undesirable contaminant in many hydrocarbon streams and volumes having hydrocarbon carbon chain lengths of from C1 to C30, some of which may be utilized as or in fuels containing hydrocarbon molecules having C1-C12.

Future gasoline specifications in the United States require sulfur compounds to be reduced to very low levels. The levels are low enough that gasoline blend components such as butanes containing sulfur compounds will make the finished gasoline fail sulfur limits. Refiners desire to limit their capital expenditures and seek alternatives to the building of additional hydrotreating capacity, so they are seeking alternatives to remove these sulfur compounds from their distillates.

It would be desirable to remove sulfur compounds from refinery distillate streams and other hydrocarbon and/or hydrogen streams and volumes using an alternative process to those presently in use.

SUMMARY

There is provided in one non-limiting embodiment a method for removing hydrogen sulfide from a hydrogen and/or hydrocarbon stream containing the hydrogen sulfide. The method includes contacting the stream with an additive, where the additive comprises from 0 to about 80 vol % of at least one solvent based on the total amount of additive and at least one alkyl carbonate in an amount effective to react with the hydrogen sulfide to form at least one reaction product in a treated stream.

In an alternative non-restrictive version there is provided a treated stream that includes hydrocarbons and optionally hydrogen; hydrogen sulfide; and an additive comprising from 0 to about 80 vol % of at least one solvent based on the total amount of additive; and at least one alkyl carbonate where the at least one alkyl carbonate is present in an amount effective to react with the hydrogen sulfide to form at least one reaction product in a treated stream. In another non-limiting embodiment the treated stream only contains reaction products of the alkyl carbonate with $H_2S$, and does not contain appreciable amounts of $H_2S$ per se.

DETAILED DESCRIPTION

It has been discovered that treatment of certain volumes and streams generally containing hydrocarbons, particularly refinery distillates, but optionally also including hydrogen ($H_2$) with an additive comprising at least one alkyl carbonate, with or without a solvent, results in the reduction of $H_2S$ that is present to give easily removed alkyl sulfides and/or mercaptans. The optional hydrogen would be in the form of hydrogen gas. The treatment converts the hydrogen sulfide ($H_2S$) into alkyl sulfides or low molecular weight mercaptans that can be extracted from the distillate with caustic solutions, mercaptan scavengers or solid absorbents such as clay or activated carbon or liquid absorbents, such as aqueous aldehydes. More specifically, the alkyl carbonates are alkylating agents which transfer the alkyl group to the sulfur and thereby make a mercaptan or alkyl sulfide as reaction products, depending on the amount of scavenger added.

In one expected non-restrictive practice, the additive is injected into the stream or volume (e.g. distillate) in run-down lines from refinery production units to tankage and/or can be injected in recirculation loops of storage tanks. Good mixing of the additive with the distillate is helpful to facilitate reaction and additionally there needs to be a downstream separation point to remove the aqueous solution. Separators, centrifuges or even storage tank bottoms are all adequate to collect the aqueous by-products. Optionally passing the treated and dehydrated hydrocarbon through a subsequent filtration or in contact with a solid or liquid absorbent (in non-limiting embodiments, clays, carbon, zeolites, amine-aldehyde condensates and the like) removes any residual additive and the reaction products yielding lower sulfur content distillate able to meet all sales specifications. Alternatively, the separation could also be accomplished using an extraction technique such as a contact tower or caustic wash unit.

In another non-limiting embodiment with more specificity, a solution of an alkyl carbonate is injected into a stream or volume of a hydrocarbon containing $H_2S$. The alkyl carbonate is thought to reduce the $H_2S$ to low molecular weight mercaptans or alkyl sulfides which are then removed from the stream or volume by a caustic or alternatively by adding mercaptan scavenger (including, but not necessarily limited to, metal carboxylates such as those including the metals Zn, Cu, and/or Fe; oxides, hydroxides or carbonates) to the distillate. These subsequent mercaptan or alkyl sulfide scavengers should be aqueous or alternatively formulated in a hydrocarbon insoluble solvent so the sulfur-containing reaction products can be separated from the hydrocarbon stream or volume. Any separation equipment used for oil/water separation can be used in the process described herein.

A subsequent or final step may be where the treated hydrocarbon is passed through and/or contacted with an absorbent that is used to remove any residual sulfur compound or $H_2S$ scavenger to yield a hydrocarbon distillate with a much reduced $H_2S$ content.

The at least one alkyl carbonate has the formula ROC(=O)OR', where R and R' are independently C1-C18 alkyl, alkaryl, hydroxyalkyl or aryl, or where R and R' are joined to form a cyclic alkyl carbonate optionally having one or more substituents selected from the group consisting of one or more aryl groups, one or more hydroxy groups, and/or one or more branched alkyl groups. For instance, when R and R' are joined to form a cyclic alkyl carbonate they encompass ethylene carbonate and propylene carbonate, which have the respective structures:

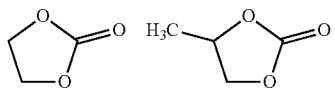

Alternatively, R and R' may independently have 1-12 carbon atoms, and alternatively may have 1-8 carbon atoms, and in another non-limiting embodiment may have from 1-4 carbon atoms. These alkyl carbonates may also be called carbonate esters.

The alkyl sulfides and/or mercaptans formed by the reaction of the alkyl carbonates with $H_2S$ may be removed via simple gravity separation of an aqueous or other immiscible phase or by use of solid absorbent beds such as metals (zinc, iron, and the like) on absorbents (clay, zeolites, carbon, and the like). Alternatively the alkyl sulfides and/or mercaptans may be removed by contact with liquid absorbents including, but not necessarily limited to, amine-aldehyde condensates and/or aqueous aldehydes, and the like. Treatment can be in stages or a single process.

Suitable $H_2S$-containing refinery distillate streams include, but are not necessarily limited to, hydrogen gas ($H_2$) per se, liquid or gas hydrocarbons selected from the group consisting of C1 to C12 alkanes, including methane, C2 to C12 alkenes, liquefied petroleum gas, natural gas, fuel gas, flare gas, naphtha, gasoline, kerosene and mixtures thereof; possibly up to C16 for diesel fuels. Fuel gas applications require treatment of gas streams that are a combination of hydrogen, C1-C4 hydrocarbons, $H_2S$, and $CO_2$. It has been discovered that the $H_2S$ scavengers described herein can remove $H_2S$ in the presence of $CO_2$ without removing the $CO_2$ or without substantially removing $CO_2$ This is an advantage of this scavenger and method because relatively less scavenger is needed to treat the system. $CO_2$ is a stronger acid than $H_2S$ therefore many amine-based scavengers will react preferentially with the $CO_2$. The selectivity of these scavengers for $H_2S$ in the presence of $CO_2$ is an advantage in reducing the amount of scavenger needed. Other advantages include the absence of scale formation and the absence of amine carbonate solids formed with the present method. It is expected that the alkyl carbonates described herein will be soluble and/or dispersible in most of the systems described, and will not form solids. Further, the methods described herein are expected to also be effective in oilfield applications, including, but not necessarily limited to, removing sulfur compounds from oilfield condensates, natural gas, and the like. The methods described herein may also be effective in treating natural gas liquids (NGL) or liquid petroleum gas (LPG) within or as it is withdrawn from a storage facility.

Water is the typical solvent for the alkyl carbonate, whereas other solvents may include, but are not necessarily limited to, C1-C8 mono- and polyhydric alcohols including, but not particularly restricted to, methanol (MeOH), ethanol, 2-propanol, butanol, 2-ethylhexanol, ethylene glycol, diethylene glycol, and glycerol. In one suitable non-limiting embodiment the solvent is methanol. Other suitable solvents include, but are not necessarily limited to, aromatic solvents, kerosene, and combinations of all of these. Suitable aromatic solvents include, but are not necessarily limited to toluene, xylene, aromatic 100, aromatic 150, aromatic 200, and the like.

In a non-limiting embodiment, the amount of solvent in the additive is a minimum of 0 vol % co-solvent (e.g. alcohol) (alkyl carbonate alone) independently to a maximum of 80 vol % co-solvent (e.g. alcohol) in the blend; in another non-restrictive version from about 10 vol % independently to about 70 vol %, alternatively from about 20 vol % independently to about 60 vol % methanol in the blend.

The effective amount of alkyl carbonate added is any amount that is effective to bind up and/or react with the $H_2S$ and at least partially convert it to a reaction product that can be removed. In one non-restrictive version, the effective amount of the alkyl carbonate is from about 1 independently to about 20 ppm alkyl carbonate per ppm $H_2S$; in a different non-limiting version from about 3 independently to about 15 ppm carbonate per ppm $H_2S$; alternatively from about 5 independently to about 10 ppm. It should be noted that the term "removed" simply means the hydrocarbon no longer contains $H_2S$. The reaction products of $H_2S$ and carbonate may still be in the hydrocarbon, but the oil is free of $H_2S$. Further, the word "independently" as used with respect to a range herein means that any lower threshold may be used with any upper threshold to provide a suitable alternative range.

In some cases, the alkyl carbonate solution will be contacted with the hydrocarbon and/or hydrogen stream and it will be both scavenger which converts the sulfur compounds present into another form and it will also be the solution which extracts the sulfur compounds formed (reaction products) away from the hydrocarbon, that is, in a single step. In other, different cases, a second treatment of the hydrocarbon stream or volume with a solid or liquid absorbent will be conducted to remove the sulfur compounds formed by the alkyl carbonate (reaction products). That is, in some non-limiting embodiments the hydrocarbon will simply be contacted with the alkyl carbonate solution and it will be both scavenger and absorbent. In other different, non-restrictive embodiments, the treated hydrocarbon will be passed through the solid/liquid absorbent to be sure all sulfur compounds (and scavenger) are removed. With respect to dose rates, if the alkyl carbonate solution may be simply injected into a hydrogen gas and/or hydrocarbon stream or volume, a ppm of scavenger to ppm of $H_2S$ ratio based on the chemistry may be provided. However if the hydrocarbon is bubbled through a solution of the alkyl carbonate then the amount of alkyl carbonate solution will be relatively large in the tower as compared with the relatively small amount of hydrocarbon and/or hydrogen gas migrating through the aqueous solution of alkyl carbonate.

For gas treating applications, such as in tower applications, where sour hydrocarbon is bubbled through the alkyl carbonate solution, the ratio will be higher as there are only small bubbles of the hydrocarbon and/or hydrogen gas migrating up through the alkyl carbonate solution in the tower. There will be a relatively large volume of the alkyl carbonate solution present since it fills the contact tower and only a relatively small amount of $H_2S$ present in the small bubbles of the hydrocarbon migrating their way through the alkyl carbonate solution. In this latter case, the ratio of alkyl carbonate to hydrocarbon can range from about 95 vol % alkyl carbonate scavenger independently to as low as 1 vol % alkyl carbonate to sour gasoline (in a non-limiting example); alternatively on the order of about 10 independently to about 50 vol % alkyl carbonate solution to sour hydrocarbon.

Generally, the alkyl carbonate will be present at a level in the treated refinery distillate stream such that the concentration of $H_2S$ in the stream is lowered to from about 1 or less than 1 independently to about 5 ppm. In other embodiments the concentration after treatment is from about 0.1 independently to about 100 ppm. In one non-limiting embodiment, there may remain from about 1 to about 2 ppm $H_2S$ in the treated hydrocarbon and gasoline specifications may still be met. In one non-limiting embodiment the highest levels of $H_2S$ expected to be treated in the hydrocarbon stream will be on the order of 500 ppm and it may be desired to reduce $H_2S$ content to less than 1 ppm. Alternatively an expected starting sulfur content of 100 ppm or less which can be reduced to 3 ppm or less, and in a different non-restrictive version the starting sulfur content may be about 50 or less, which can be reduced to 5 ppm or less.

The temperature range for the contacting by the alkyl carbonate will only be limited by the additive properties. The stream being treated cannot be so hot that the water in the additive is flashed off and leave solid alkyl carbonate behind. Conversely, the stream cannot be so cold that the additive freezes and does not mix with the hydrocarbon stream. In general, it is expected that relatively hotter will be better than relatively colder since kinetics improve as temperature increases, but again in general, the temperature cannot be so hot that the solvent (water) flashes off.

In addition to the additives already described, the additives used herein may include other compounds known to be useful in sulfur compound removal methods such as dispersants, defoamers, and the like. Any compound that does not have an undesirable interaction with the additive's ability to reduce or remove the sulfur compound may be used with at least some embodiment of the methods and compositions described herein. A defoamer in particular might be used if a gas is being treated. Additionally, a demulsifier may be employed if the separation step used involves settling in a storage tank. For instance, there could be some emulsion present that was generated by contact of the aqueous and hydrocarbon phases. A demulsifier will help break the water away from the hydrocarbon. However, as noted, in one non-limiting embodiment the method is practiced in the absence of nitrogen-containing compounds. In another non-restrictive version, the method is practiced in the absence of zinc carbonate or the absence of added zinc carbonate.

To reduce the sulfur content of the treated refinery distillate stream, a separation step is required in some non-limiting embodiments. The separation can utilize solid absorbents like carbon, clay and zeolites or alternatively the separation can utilize an extraction with caustic solutions or water. The extraction solvent can optionally be part of the alkylene carbonate additive or it may be present in a contact tower, settling tank, water/caustic wash vessel, and the like. Small particle size absorbents (powdered carbon vs. carbon pellets) are advantageous in an absorbent. Suitable powders may have a particle size of equal to or less than 0.075 mm, suitable granular sizes may have a particle size of 1.2-1.4 mm and suitable pellets may have a minimum size of 4 mm. The only necessary condition for an extraction solvent is that it should have a pH of neutral or basic (i.e. equal to or greater than 7.0). Suitable clays include, but are not necessarily limited to, attapulgite, montmorillonite, bentonite, and the like.

It was found that the process described herein does not appreciably remove any mercaptans that may be present in the streams or volumes. The high degree of selectivity toward $H_2S$ is beneficial. In many cases customers want to remove the $H_2S$ for safety reasons but mercaptans are less of an issue. If the scavenger was not selective for $H_2S$ then dose rates would have to be higher and the economics of the method would suffer.

The following examples are provided to illustrate the present method. The examples are not intended to limit the scope of the present method and they should not be so interpreted. Amounts are in weight parts or weight percentages unless otherwise indicated.

$H_2S$ SCAVENGER EXAMPLES 1-3

The Test Conditions for Examples 1-3 are as follows: A 50 ml sample of ISOPAR™ isoparaffinic solvent containing the listed amount of $H_2S$ (representing a hydrocarbon stream or volume) was treated with 100 ppm of dimethyl carbonate. Samples were stored at room temperature for the designated period and then analyzed by the UOP 163 test method (titration with $AgNO_3$) for liquid sulfide/mercaptan content. The results are listed in Table I below. Tests #2 & 3 were both run over a weekend (72 hrs) at room temperature. The only difference between the two was the amount of $H_2S$ in the hydrocarbon. Test #1 was only run for 24 hours. The dimethylcarbonate was also tested for mercaptan removal performance. Test #1 (24 hr storage of treated ISOPAR at room temp) was conducted with ethane thiol instead of H2S in an evaluation. The untreated ISOPAR had 130 ppm ethane thiol and the sample treated with 100 ppm dimethylcarbonate still had 123 ppm ethane thiol after 24 hrs at room temperature indicating very little mercaptan removal.

TABLE I $H_2S$ Scavenger Examples 1-3

| | Sample | | |
|---|---|---|---|
| | Test # 1 ppm $H_2S$ @ 24 hrs | Test # 2 ppm $H_2S$ @ 72 hrs | Test #3 ppm $H_2S$ @ 72 hrs |
| Untreated hydrocarbon | 5 | 32 | 58 |
| Treated with 100 ppm dimethylcarbonate | 2.9 | 9 | 14 |

It may be readily seen from the results in Table I that the amount of $H_2S$ was significantly reduced using dimethylcarbonate in each of the Examples.

In the foregoing specification, the invention has been described with reference to specific embodiments thereof, and has been demonstrated as effective in providing configurations, methods, and compositions for removing $H_2S$ from streams or volumes containing hydrogen gas and/or hydrocarbons, such refinery distillate streams containing them, for instance as demonstrated in the results of Table I. However, it will be evident that various modifications and changes can be made thereto without departing from the broader scope of the invention as set forth in the appended claims. Accordingly, the specification is to be regarded in an illustrative rather than a restrictive sense. For example, the type of refinery distillate streams, the types, amounts and ratios of alkyl carbonates, reaction products, treatment procedures, solvents, co-solvents, reaction parameters, solid absorbents, liquid absorbents, and other components and/or conditions falling within the claimed parameters, but not specifically identified or tried in a particular method, are expected to be within the scope of this invention. Further, it is expected that the method may change somewhat from one application to another and still accomplish the stated purposes and goals of the methods described herein.

The present invention may suitably comprise, consist or consist essentially of the elements disclosed and may be practiced in the absence of an element not disclosed. For instance, there may be provided a method for removing hydrogen sulfide from a hydrogen and/or hydrocarbon stream containing the hydrogen sulfide, where the method comprises, consists essentially of, or consists of contacting the stream with an additive, where the additive comprises, consists essentially of, or consists of from 0 to about 80 vol % of at least one solvent based on the total amount of additive and at least one alkyl carbonate in an amount effective to react with the hydrogen sulfide to form at least one reaction product in a treated stream.

In another non-limiting instance, there may be provided a treated stream comprising, consisting essentially of, or consisting of, hydrocarbons and optionally hydrogen, hydrogen sulfide, and an additive comprising, consisting essentially of, or consisting of from 0 to about 80 vol % of at least one solvent based on the total amount of additive and at least one alkyl carbonate, where the at least one alkyl carbonate is present in an amount effective to react with the hydrogen sulfide to form at least one reaction product in a treated stream.

As used herein, the terms "comprising," "including," "containing," "characterized by," and grammatical equivalents thereof are inclusive or open-ended terms that do not exclude additional, unrecited elements or method acts, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the disclosure and such term is used in preference to the more restrictive term "is" so as to avoid any implication that other, compatible materials, structures, features and methods usable in combination therewith should or must be, excluded.

As used herein, the singular forms "a," "an," and "the" are intended to include the plural forms as well, unless the context clearly indicates otherwise.

As used herein, the term "and/or" includes any and all combinations of one or more of the associated listed items.

As used herein, relational terms, such as "first," "second," "top," "bottom," "upper," "lower," "over," "under," etc., are used for clarity and convenience in understanding the disclosure and do not connote or depend on any specific preference, orientation, or order, except where the context clearly indicates otherwise.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" in reference to a given parameter is inclusive of the stated value and has the meaning dictated by the context (e.g., it includes the degree of error associated with measurement of the given parameter).

What is claimed is:

1. A method for removing hydrogen sulfide from a hydrogen and/or hydrocarbon stream containing the hydrogen sulfide, the method comprising:
   contacting the stream with an additive, where the additive comprises:
      from 0 to about 80 vol % of at least one solvent based on the total amount of additive; and
      at least one alkyl carbonate in an amount effective to react with the hydrogen sulfide to form at least one reaction product in a treated stream;
   reacting the at least one alkyl carbonate with the hydrogen sulfide to form the at least one reaction product; and
   removing the at least one reaction product from the treated stream.

2. The method of claim 1 where the at least one alkyl carbonate has the formula ROC(=O)OR', where R and R' are independently C1-C18 alkyl, alkaryl, hydroxyalkyl or aryl, or where R and R' are joined to form a cyclic alkyl carbonate optionally having one or more substituents selected from the group consisting of one or more aryl groups, one or more hydroxy groups, and/or one or more branched alkyl groups.

3. The method of claim 1 where the stream is a hydrocarbon stream that comprises liquid or gas hydrocarbons selected from the group consisting of C1 to C12 alkanes, C2 to C12 alkenes, liquefied petroleum gas, natural gas, fuel gas, flare gas, naphtha, gas oil, gasoline, kerosene, diesel fuel, and mixtures thereof.

4. The method of claim 1 where in the additive, the at least one solvent is present and selected from the group consisting of water, mono- and polyhydric alcohols having from 1 to 8 carbon atoms, aromatic solvents, kerosene, and combinations thereof.

5. The method of claim 1 where the method has an absence of added compounds containing nitrogen.

6. The method of claim 1 where the effective amount of the at least one alkyl carbonate ranges from about 1 to about 20 ppm of alkyl carbonate per ppm of hydrogen sulfide present.

7. The method of claim 1 where the stream comprises $CO_2$ and the method does not substantially remove the $CO_2$.

8. The method of claim 1 where the at least one reaction product is selected from the group consisting of mercaptans, alkyl sulfides, and combinations thereof.

9. A method for removing hydrogen sulfide from a hydrogen and/or hydrocarbon stream containing the hydrogen sulfide, the method comprising:
   contacting the stream with a nitrogen-free additive, where the additive comprises:
      from 0 to about 80 vol % of at least one solvent based on the total amount of nitrogen-free additive; and
      at least one alkyl carbonate having the formula ROC(=O)OR', where R and R' are independently C1-C18 alkyl, alkaryl, hydroxyalkyl or aryl, or where R and R' are joined to form a cyclic alkyl carbonate optionally having one or more substituents selected from the group consisting of having one or more aryl groups, one or more hydroxy groups, and/or one or more branched alkyl groups, where the amount of the at least one alkyl carbonate is effective to react with the hydrogen sulfide to form at least one reaction product in a treated stream;

reacting the at least one alkyl carbonate with the hydrogen sulfide to form the at least one reaction product; and removing the at least one reaction product from the treated stream;

where the stream is a hydrocarbon stream that comprises liquid or gas hydrocarbons selected from the group consisting of C1 to C12 alkanes, C2 to C12 alkenes, liquefied petroleum gas, natural gas, fuel gas, flare gas, naphtha, gas oil, gasoline, kerosene, diesel fuel, and mixtures thereof.

10. The method of claim 9 where the at least one solvent is present and is selected from the group consisting of water, mono- and polyhydric alcohols having from 1 to 8 carbon atoms, aromatic solvents, kerosene, and combinations thereof.

11. The method of claim 9 where the method has an absence of added compounds containing nitrogen.

12. The method of claim 9 where the effective amount of the at least one alkyl carbonate ranges from about 1 to about 20 ppm of alkyl carbonate per ppm of hydrogen sulfide present.

13. The method of claim 9 where the stream comprises $CO_2$ and the method does not substantially remove the $CO_2$.

14. A treated stream comprising:
hydrocarbons and optionally hydrogen;
hydrogen sulfide; and
an additive comprising:
from 0 to about 80 vol % of at least one solvent based on the total amount of additive;
at least one alkyl carbonate, where the at least one alkyl carbonate is present in an amount effective to react with the hydrogen sulfide to form at least one reaction product in the treated stream; and the at least one reaction product.

15. The treated stream of claim 14 where the at least one alkyl carbonate has the formula ROC(=O)OR', where R and R' are independently C1-C18 alkyl, alkaryl, hydroxyalkyl or aryl, or where R and R' are joined to form a cyclic alkyl carbonate optionally having one or more substituents selected from the group consisting of one or more aryl groups, one or more hydroxy groups, and/or one or more branched alkyl groups.

16. The treated stream of claim 14 where the treated stream is a hydrocarbon stream comprising hydrocarbons that comprise liquid or gas hydrocarbons selected from the group consisting of C1 to C12 alkanes, C2 to C12 alkenes, liquefied petroleum gas, natural gas, fuel gas, flare gas, naphtha, gas oil, gasoline, kerosene, diesel fuel, and mixtures thereof.

17. The treated stream of claim 14 where the treated stream has an absence of added compounds containing nitrogen.

18. The treated stream of claim 14 where the amount effective of the at least one alkyl carbonate ranges from about 1 to about 20 ppm of alkyl carbonate per ppm of hydrogen sulfide present.

19. The treated stream of claim 14 where the treated stream comprises $CO_2$.

* * * * *